US012626369B2

(12) United States Patent
Zhou et al.

(10) Patent No.: US 12,626,369 B2
(45) Date of Patent: May 12, 2026

(54) GABOR WAVELET-FUSED MULTI-SCALE LOCAL LEVEL SET ULTRASONIC IMAGE SEGMENTATION METHOD

(71) Applicant: Beijing Lepulmage Technology Co., Ltd., Beijing (CN)

(72) Inventors: Zhifeng Zhou, Beijing (CN); Huiling Zou, Beijing (CN)

(73) Assignee: Beijing Lepulmage Technology Co., Ltd., Beijing (CN)

( * ) Notice: Subject to any disclaimer, the term of this patent is extended or adjusted under 35 U.S.C. 154(b) by 570 days.

(21) Appl. No.: 18/048,527

(22) Filed: Oct. 21, 2022

(65) Prior Publication Data

US 2023/0070200 A1    Mar. 9, 2023

Related U.S. Application Data

(63) Continuation-in-part of application No. PCT/CN2020/107283, filed on Aug. 6, 2020.

(51) Int. Cl.
*G06K 9/00*    (2022.01)
*A61B 8/00*    (2006.01)
(Continued)

(52) U.S. Cl.
CPC ............... *G06T 7/168* (2017.01); *A61B 8/12* (2013.01); *A61B 8/54* (2013.01); *G06T 7/12* (2017.01);
(Continued)

(58) Field of Classification Search
CPC . G06T 7/168; G06T 2207/20064; G06T 7/12; G06T 2207/20161;
(Continued)

(56) References Cited

U.S. PATENT DOCUMENTS 10,521,904 B2    12/2019  Termura
2018/0289360 A1*  10/2018  Funakubo ........... G01S 7/52085

FOREIGN PATENT DOCUMENTS

CN    104504720 A    4/2015
CN    106296649 A    1/2017
(Continued)

OTHER PUBLICATIONS

Li, C., Xu, C., Gui, C., & Fox, M. D. (Jun. 2005). Level set evolution without re-initialization: a new variational formulation. In 2005 IEEE computer society conference on computer vision and pattern recognition (CVPR'05) (vol. 1, pp. 430-436). IEEE. (Year: 2005).*

(Continued)

*Primary Examiner* — Emily C Terrell
*Assistant Examiner* — Kevin M Coomber
(74) *Attorney, Agent, or Firm* — Dinsmore & Shohl LLP

(57) ABSTRACT

Disclosed is a Gabor wavelet-fused multi-scale local level set ultrasonic image segmentation method. In the method, non-uniformity of the grayscale of an ultrasonic image is taken as a texture having cluttered directions, the multi-directional property of Gabor wavelets is used to process the image, and intermediate images in different filtering directions are fused by taking maximum values, so as to obtain an intermediate image having a weakened texture effect and an enhanced difference between a foreground and a background. For the feature of a weak edge of an ultrasonic image, a concept of multi-scale is used to improve the conventional LIC method, Gaussian convolution kernels having different variances are set, and a final edge is obtained by means of average fusion.

5 Claims, 3 Drawing Sheets

(51) Int. Cl.

| | | |
|---|---|---|
| *A61B 8/12* | (2006.01) | |
| *G06T 7/12* | (2017.01) | |
| *G06T 7/168* | (2017.01) | |
| *G06T 7/174* | (2017.01) | |
| *G06V 10/40* | (2022.01) | |

(52) U.S. Cl.

CPC ............... *G06T 7/174* (2017.01); *G06V 10/40* (2022.01); *G06T 2207/10068* (2013.01); *G06T 2207/10132* (2013.01); *G06T 2207/20016* (2013.01); *G06T 2207/20064* (2013.01); *G06T 2207/20161* (2013.01); *G06T 2207/20192* (2013.01); *G06T 2207/20221* (2013.01)

(58) Field of Classification Search

CPC ... G06T 2207/20192; G06T 7/13; G06T 7/11; G06T 7/149; G06T 7/10; G06T 7/194; G06T 2207/10132; G06T 2207/10068; G06T 7/174; G06T 2207/20016; G06T 2207/20221; G06V 10/26; G06V 10/25; G06V 10/40; G06V 10/44; A61B 8/12; A61B 8/54; A61B 8/085

See application file for complete search history.

(56) References Cited

FOREIGN PATENT DOCUMENTS

| CN | 106780508 A | 5/2017 |
|---|---|---|
| CN | 107153833 A | 9/2017 |
| CN | 110084824 A | 8/2019 |

OTHER PUBLICATIONS

Zhang, L. H. (2011). Localized multi-channel level set segmentation combined with gabor texture feature. Dianzi Xuebao(Acta Electronica Sinica), 39(7), 1569-1574. (Year: 2011).*

Chen, C. I. (2017). Fusion of PET and MR brain images based on IHS and log-Gabor transforms. IEEE Sensors Journal, 17(21), 6995-7010. (Year: 2017).*

Ben Abdallah, M., Malek, J., Azar, A. T., Montesinos, P., Belmabrouk, H., Esclarín Monreal, J., & Krissian, K. (2015). Automatic extraction of blood vessels in the retinal vascular tree using multiscale medialness. International Journal of Biomedical Imaging, 2015(1), 519024. (Year: 2015).*

Redondo, R., Šroubek, F., Fischer, S., & Cristóbal, G. (2009). Multifocus image fusion using the log-Gabor transform and a multisize windows technique. Information Fusion, 10(2), 163-171. (Year: 2009).*

International Search Report and Written Opinion from PCT/CN2020/107283 mailed Jan. 26, 2021, 17 pages.

Sandberg et al., A Level-Set and Gabor-based Active Contour Algorithm for Segmenting Textured Images, ResearchGate, https://www.researchgate.net/publication/2848498, Jan. 8, 2016, 11 pages.

Li et al., Image Segmentation Based on Multi-Direction Gabor Filters, Foreign Electronic Measurement Technology, vol. 36, No. 3, Mar. 31, 2017, 7 pages.

Zhang et al., Localized Multi-Channel Level Set Segmentation Combined with Gabor Texture Feature, Acta Electronica Sinica, vol. 39, No. 7, Jul. 31, 2011, 20 pages.

International Search Report of PCT/CN2020/107283 mailed Jan. 26, 2021, 3 pages.

Second Office Action Dated Jan. 9, 2025 for Corresponding Chinese Patent Application No. 202080100122.1.

* cited by examiner

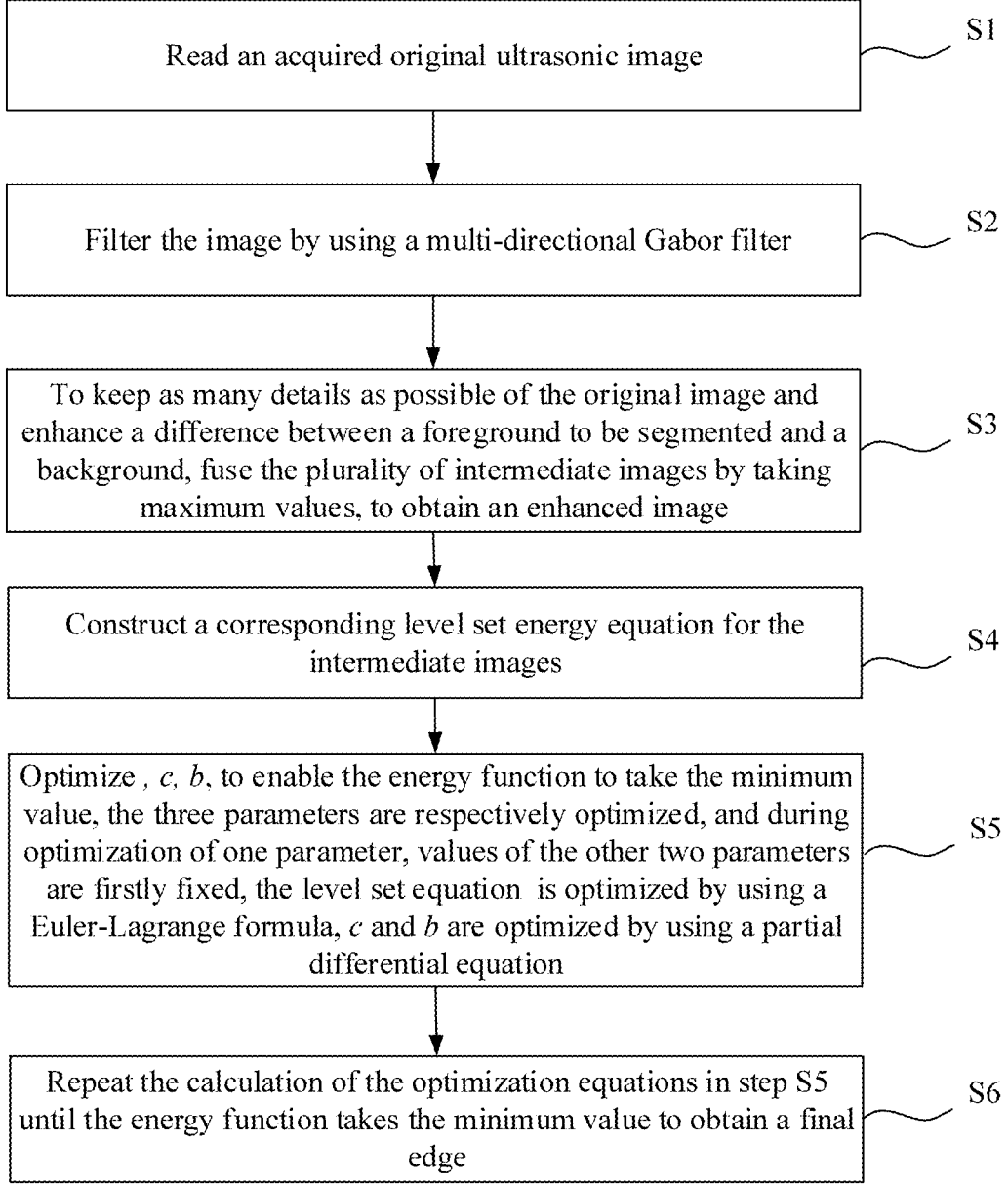

| Read an acquired original ultrasonic image | S1 |

| Filter the image by using a multi-directional Gabor filter | S2 |

| To keep as many details as possible of the original image and enhance a difference between a foreground to be segmented and a background, fuse the plurality of intermediate images by taking maximum values, to obtain an enhanced image | S3 |

| Construct a corresponding level set energy equation for the intermediate images | S4 |

| Optimize , $c$, $b$, to enable the energy function to take the minimum value, the three parameters are respectively optimized, and during optimization of one parameter, values of the other two parameters are firstly fixed, the level set equation is optimized by using a Euler-Lagrange formula, $c$ and $b$ are optimized by using a partial differential equation | S5 |

| Repeat the calculation of the optimization equations in step S5 until the energy function takes the minimum value to obtain a final edge | S6 |

FIG. 4

GABOR WAVELET-FUSED MULTI-SCALE LOCAL LEVEL SET ULTRASONIC IMAGE SEGMENTATION METHOD

CROSS-REFERENCE TO RELATED APPLICATION

This application is a continuation-in-part of International Application No. PCT/CN2020/107283, filed on Aug. 6, 2020, the entire contents of which is incorporated herein by reference.

FIELD

The present application relates to the field of ultrasonic image segmentation, and in particular to a Gabor wavelet-fused multi-scale local level set ultrasonic image segmentation method.

BACKGROUND

Currently, tumors in the digestive tract have high incidence worldwide and have a high fatality rate, which seriously threaten people's life and health. Ultrasonic endoscopy uses ultrasound to detect and image the internal organs of human body, which is non-damaging to human body and has low cost of detection and high diagnostic accuracy, and therefore becomes one of the important means for early detection and treatment of digestive tract tumors. The location, size, and shape of a tumor in the digestive tract are important parameters to assist physicians in judgment. Therefore, it is of great significance to perform edge extraction of tumors on ultrasonic images. Due to the detection characteristics of an ultrasound system, ultrasonic images have the disadvantages of uneven grayscale distribution, high noise, and poor edge continuity. As a result, it is difficult to obtain complete and accurate edges by using some classical segmentation methods such as a Canny operator method and a thresholding method.

The proposal of an active contour model is a breakthrough in the field of image segmentation. The basic idea of the proposal is to use continuous curves to fit edges to be measured and to perform image segmentation by defining an energy functional equation with the edges as variables and taking minimum values. With the introduction of a level set method, the applicability of the active contour model has been developed. However, the conventional level set algorithm still has some defects when performing actual image processing. For example, the famous Mumford-Shah model is not appropriate for actual application due to the complex computational iteration process and massive computation. It is also difficult to obtain accurate segmentation results for images having non-uniform grayscale by using the Chan-Vase model improved based on this model.

A local area-based level set method has been proposed for the segmentation of images having non-uniform grayscale. In 2007, Li proposed the local binary energy (local binary pattern, LBF) model, which introduced a Gaussian kernel function into an energy equation to extract local grayscale information, and added a regularization item, so that reinitialization is not required during the iteration of a level set, thereby reducing the amount of operations. However, the algorithm is sensitive to an initial contour and has poor robustness to noisy images. In 2008, Lankton proposed the LRB method, which also uses local region information to segment inhomogeneous images. However, the computational efficiency of the algorithm is low. In 2011, Li proposed the local intensity clustering level set method, which has a good segmentation effect for images with uniform grayscale variation but has serious over-segmentation for ultrasonic images with weak edges and uneven grayscale variation.

Therefore, there is a need in this field for a method that can accurately segment ultrasonic images.

SUMMARY

For the foregoing technical problems in the prior art, an objective of the present application is to provide an ultrasonic image segmentation algorithm, thereby improving the segmentation accuracy of ultrasonic images.

The technical solution of the present application is as follows.

A first aspect of the present application provides an image segmentation method, including the following steps:

step S1: obtaining an original image to be processed;

step S2: performing filtering decomposition on the original image by using multi-directional Gabor wavelets, to obtain a plurality of intermediate images;

step S3: fusing the plurality of intermediate images by taking maximum values, to obtain an enhanced image;

step S4: constructing a corresponding level set energy equation for the intermediate images;

step S5: optimizing parameters of the energy equation to enable an energy function to take a minimum value, to obtain an accurate position of an edge; and step S6: repeating step S5 until the energy function takes the minimum value to obtain a final edge.

Preferably, a change function of the multi-directional Gabor wavelets in step S2 is:

$$g_q(x,y)=g(x \cos \theta+y \sin \theta,-x \sin \theta+y \cos \theta),$$

where g(x,y) is a Gabor function in a two-dimensional space; $g_q(x,y)$ is a multi-directional Gabor wavelet transformation template, where x and y are coordinates in two directions of the template; $\theta=q\pi/Q$, $Q$ represents a total quantity of directions in wavelet transformation, and q is a direction parameter; and convolution is performed on Gabor wavelets in different directions with the original image to obtain the plurality of intermediate images, as shown by the following formula:

$$I_q(x,y)=I(x,y)*g_q(x,y)q=0,1, \ldots Q-1$$

where I(x,y) is original image data, and $I_q(x,y)$ is intermediate image data.

Preferably, a fusion equation for fusing the plurality of intermediate images in step S3 is as follows:

$$I'(x,y)=\max\{I_q(x,y),q=0,1, \ldots, Q-1\},$$

where I'(x,y) is fused image data.

Preferably, the energy equation includes: an energy functional item related to the image itself, a length regularization item for keeping edge smoothness by limiting an edge length, and a distance regularization item for keeping a level set equation from reinitialization.

Preferably, it is assumed that an image having non-uniform grayscale is a result obtained after a grayscale offset item and an actual image are weighted and summed with noise added therein, and Gaussian templates having different variances are constructed to calculate the energy functional item; and the Gaussian templates are as follows:

$$K_{\sigma_p}(u) = \begin{cases} \dfrac{1}{a}e^{-|u|^2/2\sigma_p^2}, & |u| \leq \rho, \\ 0, & |u| > \rho \end{cases}$$

where $\sigma_p = \sigma_0 \times p$; $\sigma_p$ is a variance of a different scale, and $\sigma_0$ is a minimum variance, $K_{\sigma_p}(u)$ is a Gaussian filter kernel having a different variance, and p is a different scale and the form of the energy equation is as follows:

$$\mathcal{F}_{(\phi,c,b)} = \varepsilon(\phi,c,b) + \nu\mathcal{L}_{(\phi)} + \mu\mathcal{R}_{(\phi)},$$

where $\mathcal{F}(\phi, c, b)$ is a constructed energy function, $\varepsilon(\phi, c, b)$ is the energy functional item related to the image itself, $L(\phi)$ is the length regularization item used for forcing level set contour to be smooth by limiting an arc length thereof, $R(\phi)$ is the distance regularization item that keeps a level set function stable during iteration in order to keep a level set from reinitialization, and $\nu$ and $\mu$ are respectively corresponding weighting factors;

$$\varepsilon = \frac{1}{P}\int\sum_{p=1}^{P}\sum_{i=1}^{2}\left(\int K_{\sigma_p}(y-x)|I'(x) - b_p(y)c_{i,p}|^2 dy\right)(M_i(\phi(x)))dx,$$

where P is a quantity of different scales, $K_{\sigma_p}(u)$ is a multi-scale circular neighborhood template, $b_p$ is a grayscale offset field calculated in the scale p; and $c_{i,p}$ is an image corrected by using the grayscale offset field in the scale p, $M_1(\phi) = H(\phi)$, and $M_2(\phi) = 1 \parallel H(\phi)$; and H(x) is a Heaviside function; $M_1(\phi)$ and $M_2(\phi)$ respectively correspond to an edge inside and an edge outside of the image.

$L(\phi)$ and $R_p(\phi)$ are the two regularization items, $L(\phi)$ is the length regularization item used for calculating a length of a zero-level contour of a level set equation $\phi$ and forcing level set contour to be smooth by limiting an arc length thereof; and an expression of the length regularization item is as follows:

$$\mathcal{L}_{(\phi)} = \int|\nabla H(\phi)|dx$$

$R(\phi)$ is the distance regularization item that keeps a level set function stable during iteration in order to keep a level set from reinitialization, and an expression of the distance regularization item is as follows:

$$\mathcal{R}(\phi) = \int p(|\nabla\phi|)dx$$

$$p(s) = \begin{cases} \dfrac{1}{(2\pi)^2}(1-\cos(2\pi s)), & s \leq 1 \\ \dfrac{1}{2}(s-1)^2, & s \geq 1 \end{cases},$$

where p(s) represents a part of a regularization item equation, where s represents the absolute value of an edge gradient of the image.

Preferably, $\phi$, c, b are optimized to enable the energy function to take the minimum value, the three parameters are respectively optimized, and during optimization of one parameter, values of the other two parameters are firstly fixed, the level set equation $\phi$ is optimized by using a Euler-Lagrange formula, c and b are optimized by using a partial differential equation, and an optimization equation for $\phi$ is as follows:

$$\frac{\partial\phi}{\partial t} = -\frac{1}{P}\delta(\phi)\sum_{p=0}^{P-1}(e_{1,p} - e_{2,p}) + \nu\delta(\phi)div\left(\frac{\nabla\phi}{|\nabla\phi|}\right) + \mu div(d(|\nabla\phi|)\nabla\phi),$$

$$e_{i,p} = \int K_{\sigma_p}(y-x)|I(x) - b_p(y)c_{i,p}|^2 dy,$$

$$i = 1,2,$$

$$\frac{\partial\phi}{\partial t}$$

represents performing iteration on the level set equation, P represents a scale, $\delta(\phi)$ is an impulse function, and $\nu$ and $\mu$ respectively represent the corresponding weighting factors, and div represents a difference operation; $e_{i,p}$ is an energy factor related to a distance constructed in a different scale; and $\phi$ and b are fixed, and c is optimized by the following equation:

$$c_{i,p} = \frac{\int(b_p * K_{\sigma_p}) * I * M_i(\phi(y))dy}{\int(b_p^2 * K_{\sigma_p})M_i(\phi(y))dy}, i = 1,2,$$

where $b_p$ is a grayscale offset field calculated in the scale p; and $c_{i,p}$ is an image corrected by using the grayscale offset field in the scale p, and includes an inside part and an outside part of the level set; $\phi$ and c are fixed, and b is optimized by the following equation:

$$b_p = \frac{(I \cdot \Sigma_{i=1}^2 c_{i,p}M_i(\phi(y))) * K_{\sigma_p}}{(\Sigma_{i=1}^2 c_{i,p}^2 M_i(\phi(y))) * K_{\sigma_p}},$$

where $b_p$ is the grayscale offset field calculated in the scale p, and $K_{\sigma_p}$ is the Gaussian filter kernel having a different variance.

A second aspect of the present application provides an image processing apparatus is provided, including:

a storage part, configured to store an image to be processed; and a processing part, configured to obtain edge information in the image in the storage apparatus by using the method in any of the foregoing solutions.

A third aspect of the present application provides an ultrasonic imaging apparatus is provided, including:

an ultrasonic probe, configured to emit an ultrasonic wave to an object under test, receive a reflected ultrasonic wave reflected by the object under test, and generate an echo signal corresponding to the reflected ultrasonic wave;

a generation part, configured to generate an ultrasonic image related to the object under test according to the echo signal; and a processing part, configured to obtain edge information in the ultrasonic image by using the method by using the method in any of the foregoing solutions.

A fourth aspect of the present application provides an ultrasonic endoscope, including an insertion part, a control part, and the ultrasonic imaging apparatus according to the third aspect of the present application.

Through the foregoing technical solution, the present application provides a Gabor wavelet-fused multi-scale local clustering level set ultrasonic image segmentation method. The multi-directional property of Gabor wavelets is used to process images having non-uniform grayscale, and an intermediate image with an enhanced difference between a region to be segmented and a background is obtained by fusing maximum values. In the present application, the multi-scale idea is introduced into a local clustering level set algorithm, Gaussian kernel functions having different variances are set, and a level set is iterated by means of average fusion to obtain a final edge, thereby overcoming the disadvantages of a weak edge and inaccurate segmentation of an ultrasonic image.

BRIEF DESCRIPTION OF THE DRAWINGS

FIG. 4 is another schematic flowchart of an image segmentation method according to the present application.

DETAILED DESCRIPTION

An image segmentation method, an image processing apparatus, and an ultrasonic imaging apparatus according to the present application are described below with reference to the accompanying drawings.

Embodiment 1

Figure 1:
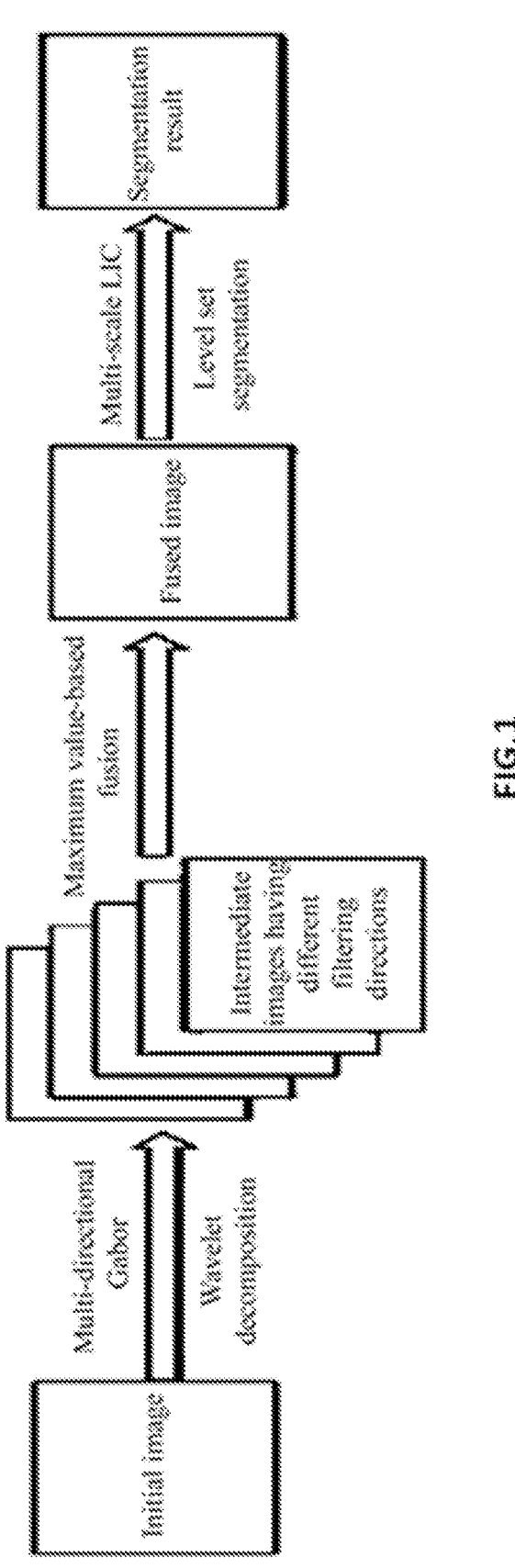
FIG. 1 is a schematic flowchart of an image segmentation method according to the present application.

An implementation procedure of the image segmentation method in this embodiment is shown in FIG. 1 and FIG. 4.

Step 1: Read an acquired original ultrasonic image. In a preferred embodiment, the ultrasonic image is a two-dimensional ultrasonic image of a stomach cross-section.

Step 2: Filter the image by using a multi-directional Gabor filter. A Gabor function in a two-dimensional space is shown in the following formula:

$$g(x, y) = \frac{1}{2\pi\sigma_x\sigma_y}\exp\left[-\frac{1}{2}\left(\frac{x^2}{\sigma_x^2} + \frac{y^2}{\sigma_y^2}\right)\right] \times \exp(2\pi jWx).$$

In the formula, $\sigma_x$ and $\sigma_y$ respectively represent broadenings of a Gaussian function in an x direction and a y direction, and W represents a frequency bandwidth of a Gabor wavelet. A multi-directional Gabor wavelet transformation function may be represented as:

$$g_q(x,y)=g(x \cos \theta+y \sin \theta,-x \sin \theta+y \cos \theta)$$

where, $g(x,y)$ is a Gabor function in a two-dimensional space; $g_q(x,y)$ is a multi-directional Gabor wavelet transformation template, where x and y are coordinates in two directions of the template; $\theta=q\pi/Q$, and $Q$ represents a total quantity of directions in wavelet transformation; and convolution is performed on Gabor wavelets in different directions with the original image to obtain the plurality of intermediate images, as shown by the following formula:

$$I_q(x,y)=I(x,y)*g_q(x,y) q=0,1, \ldots Q-1,$$

$I(x,y)$ is the original image data and $I_q(x,y)$ is intermediate image data.

Step S3: To keep as many details as possible of the original image and enhance a difference between a foreground to be segmented and a background, fuse the plurality of intermediate images by taking maximum values, to obtain an enhanced image.

$$I'(x,y)=\max\{I_q(x,y),q=0,1, \ldots , Q-1\},$$

where $I'(x,y)$ is the fused image data.

Step S4: Construct a corresponding level set energy equation for the intermediate images. The energy equation of the entire image is formed by three parts, which include: an energy functional item related to the image itself, a length regularization item for keeping edge smoothness by limiting an edge length, and a distance regularization item for keeping a level set equation from reinitialization. It is assumed that an image having non-uniform grayscale is a result obtained after a grayscale offset item and an actual image are weighted and summed with noise added therein, and Gaussian templates having different variances are constructed to calculate the energy functional item. The Gaussian templates are as follows:

$$K_{\sigma_p}(u) = \begin{cases} \dfrac{1}{a}e^{-|u|^2/2\sigma_p^2}, & |u| \leq \rho, \\ 0 & |u| > \rho \end{cases}$$

where $\sigma_p=\sigma_0\times p$, $\sigma_p$ is a variance of a different scale, and $\sigma_0$ is a minimum variance, and p is the different scale, $K_{\sigma_p}$ is a Gaussian filter kernel having a different variance. The form of the entire energy equation is as follows:

$$\mathcal{F}(\phi,c,b)=\varepsilon(\phi,c,b)+v\mathcal{L}(\phi)+\mu\mathcal{R}(\phi),$$

where $\mathcal{F}(\phi,c,b)$ is a constructed energy function, $\varepsilon(\phi, c, b)$ is the energy functional item related to the image itself, $L(\phi)$ is the length regularization item used for forcing level set contour to be smooth by limiting an arc length thereof, $R(\phi)$ is the distance regularization item that keeps a level set function stable during iteration in order to keep a level set from reinitialization, and $v$ and $\mu$ are respectively corresponding weighting factors;

$$\varepsilon = \frac{1}{P}\int\sum_{p=1}^{P}\sum_{i=1}^{2}\left(\int K_{\sigma_p}(y-x)|I'(x)-b_p(y)c_{i,p}|^2 dy\right)(M_i(\phi(x)))dx,$$

where P is a quantity of different scales, $M_1(\phi)=H(\phi)$, $M_2(\phi)=1-H(\phi)$. H(x) is a Heaviside function. $M_1(\phi)$ and $M_2(\phi)$ respectively correspond to an edge inside and an edge outside of the image. In the formula, $\mathcal{L}(\phi)=\int|\nabla H(\phi)|dx$, $\mathcal{R}(\phi)=\int p(|\nabla\phi|)dx$. A functional form of p(s) is as follows:

$$p(s) = \begin{cases} \dfrac{1}{(2\pi)^2}(1 - \cos(2\pi s)), & s \leq 1 \\ \dfrac{1}{2}(s - 1)^2, & s \geq 1 \end{cases}$$

where p(s) represents a part of a regularization item equation, where s represents the absolute value of an edge gradient of the image.

Step 5: Optimize $\phi$, c, b, to enable the energy function to take the minimum value, the three parameters are respectively optimized, and during optimization of one parameter, values of the other two parameters are firstly fixed, the level set equation $\phi$ is optimized by using a Euler-Lagrange formula, c and b are optimized by using a partial differential equation, and an optimization equation for $\phi$ is as follows:

$$\frac{\partial \phi}{\partial t} = -\frac{1}{P}\delta(\phi)\sum_{p=0}^{P-1}(e_{1,p} - e_{2,p}) + v\delta(\phi)div\left(\frac{\nabla \phi}{|\nabla \phi|}\right) + \mu div(d(|\nabla \phi|)\nabla \phi)$$

$$e_{i,p} = \int K_{\sigma_p}(y-x)|I(x) - b_p(y)c_{i,p}|^2 dy, \, i = 1, 2,$$

where $$\frac{\partial \phi}{\partial t}$$

represents performing iteration on the level set equation, P represents a scale, $\delta(\phi)$ is an impulse function, and $v$ and $\mu$ respectively represent the corresponding weighting factors, and div represents a difference operation; $e_{i,p}$ is an energy factor related to a distance constructed in a different scale; and $\phi$ and b are fixed, and c is optimized by the following equation:

$$c_{i,p} = \frac{\int \left(b_p * K_{\sigma_p}\right) * I * M_i(\phi(y))dy}{\int \left(b_p^2 * K_{\sigma_p}\right)M_i(\phi(y))dy}, \, i = 1, 2,$$

where $b_p$ is a grayscale offset field calculated in the scale p; and $c_{i,p}$ is an image corrected by using the grayscale offset field in the scale p, and includes an inside part and an outside part of the level set;
$\phi$ and c are fixed, and b is optimized by the following equation:

$$b_p = \frac{\left(I \cdot \sum_{i=1}^{2} c_{i,p}M_i(\phi(y))\right) * K_{\sigma_p}}{\left(\sum_{i=1}^{2} c_{i,p}^2 M_i(\phi(y))\right) * K_{\sigma_p}},$$

where $b_p$ is the grayscale offset field calculated in the scale p, and $K_{\sigma_p}$ is the Gaussian filter kernel having a different variance.

Step S6: Repeat the calculation of the optimization equations in step S5 until the energy function takes the minimum value to obtain a final edge.

Embodiment 2

Figure 2:
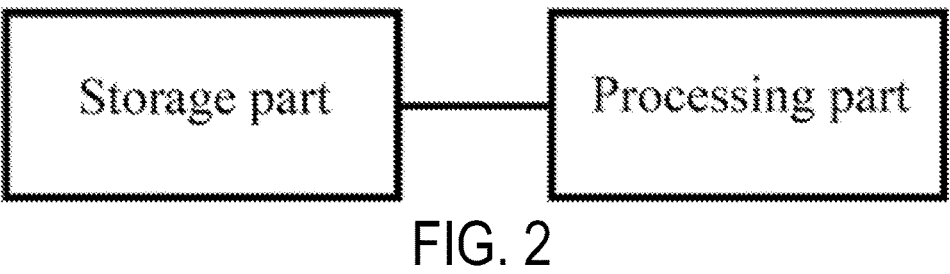
FIG. 2 is a schematic structural diagram of an image processing apparatus according to the present application.

As shown in FIG. 2, this embodiment provides an image processing apparatus, including a storage part and a processing part. The storage part is configured to store an image to be processed.

The processing part is configured to obtain edge information in the image in the storage apparatus by using the method in any implementation in Embodiment 1.

Embodiment 3

Figure 3:
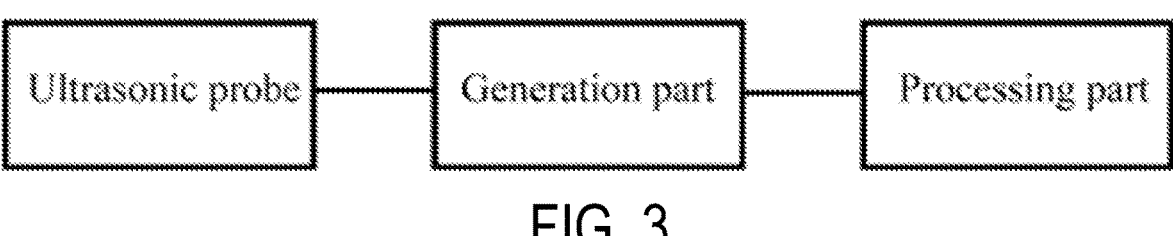
FIG. 3 is a schematic structural diagram of an ultrasonic imaging apparatus according to the present application.

As shown in FIG. 3, this embodiment provides an ultrasonic imaging apparatus, including an ultrasonic probe, a generation part, and a processing part.

The ultrasonic probe is configured to emit an ultrasonic wave to an object under test, receive a reflected ultrasonic wave reflected by the object under test, and generate an echo signal corresponding to the reflected ultrasonic wave.

The generation part is configured to generate an ultrasonic image related to the object under test according to the echo signal.

The processing part is configured to obtain edge information in the ultrasonic image by using the method in any implementation in Embodiment 1.

A person skilled in the art can understand that although the image segmentation method in the above embodiments uses an ultrasonic image as a processing object, the present application is not limited to thereto. That is, in addition to using an ultrasonic image as a processing object, the image segmentation method in the embodiments of the present application can also process various grayscale images suitable for processing by using the method, for example, a CT image generated by an X-ray computed tomography device, an X-ray image generated by an X-ray diagnostic device, and an MR image generated by a magnetic resonance imaging device.

Several embodiments of the present application are described with respect to the present application. However, these embodiments are shown as examples and are not intended to limit the scope of the present application. These new embodiments may be implemented in various other ways, and various omissions, substitutions, and changes can be made without departing from the scope of the main idea of the present application. These embodiments and variations thereof fall within the scope and the main idea of the present application and fall within the scope of the prevent application and its equivalents as set forth in the claims.

What is claimed is:
1. An image segmentation method, comprising the following steps:
    step S1: obtaining an original image to be processed;
    step S2: performing filtering decomposition on the original image by using multi-directional Gabor wavelets, to obtain a plurality of intermediate images;
    step S3: fusing the plurality of intermediate images by taking maximum values, to obtain an enhanced image;
    step S4: constructing a corresponding level set energy equation for the intermediate images;
    step S5: optimizing parameters of the energy equation to enable an energy function to take a minimum value, to obtain an accurate position of an edge; and
    step S6: repeating step S5 until the energy function takes the minimum value to obtain a final edge;
    wherein a fusion equation for fusing the plurality of intermediate images in step S3 is as follows:

$$I'(x,y) = \max\{I_q(x,y), q=0,1,\ldots,Q-1\},$$

where I'(x,y) is the fused image data.
2. The image segmentation method according to claim 1, wherein a change function of the multi-directional Gabor wavelets in step S2 is:

$$g_q(x,y) = g(x \cos \theta + y \sin \theta, -x \sin \theta + y \cos \theta),$$

wherein g(x,y) is a Gabor function in a two-dimensional space; $g_q(x,y)$ is a multi-directional Gabor wavelet transformation template, where x and y are coordinates in two directions of the template; $\theta = q\pi/Q$, Q represents a total quantity of directions in wavelet transformation, and q is a direction parameter; and convolution is performed on Gabor wavelets in different directions with the original image to obtain the plurality of intermediate images, as shown by the following formula:

$$I_q(x,y) = I(x,y) * g_q(x,y) \, q=0,1,\ldots Q-1,$$

wherein I(x,y) is original image data, and $I_q(x,y)$ is intermediate image data.

3. The image segmentation method according to claim 1, wherein the energy equation comprises: an energy functional item related to the image to be processed itself, a length regularization item for keeping edge smoothness by limiting an edge length, and a distance regularization item for keeping a level set equation from reinitialization.

4. An image processing apparatus, comprising:
a storage medium configured to store an image to be processed; and
a processor configured to:
    obtain the image to be processed from the storage medium;
    perform filtering decomposition on the original image by using multi-directional Gabor wavelets, to obtain a plurality of intermediate images;
    fuse the plurality of intermediate images by taking maximum values, to obtain an enhanced image;
    construct a corresponding level set energy equation for the intermediate images;
    optimize parameters of the energy equation to enable an energy function to take a minimum value, to obtain an accurate position of an edge; and
    repeat optimizing the parameters of the energy equation until the energy function takes the minimum value to obtain a final edge.

5. An ultrasonic imaging apparatus, comprising:
an ultrasonic probe configured to emit an ultrasonic wave to an object under test, receive a reflected ultrasonic wave reflected by the object under test, and generate an echo signal corresponding to the reflected ultrasonic wave;
a generation part configured to generate an ultrasonic image related to the object under test according to the echo signal; and
a processing part configured to:
    obtain the image to be processed from the storage medium;
    perform filtering decomposition on the original image by using multi-directional Gabor wavelets, to obtain a plurality of intermediate images;
    fuse the plurality of intermediate images by taking maximum values, to obtain an enhanced image;
    construct a corresponding level set energy equation for the intermediate images;
    optimize parameters of the energy equation to enable an energy function to take a minimum value, to obtain an accurate position of an edge; and
    repeat optimizing the parameters of the energy equation until the energy function takes the minimum value to obtain a final edge.

* * * * *